United States Patent [19]

Dannels et al.

[11] Patent Number: 4,808,760
[45] Date of Patent: Feb. 28, 1989

[54] TELOMERS PREPARED FROM CHLOROTRIFLUOROETHYLENE AND 1,2-DIBROMO-2-CHLOROTRIFLUOROETHANE

[75] Inventors: Bobby F. Dannels; Michael J. Fifolt, both of Grand Island; David Y. Tang, East Amherst, all of N.Y.

[73] Assignee: Occidental Chemical Corporation, Niagara Falls, N.Y.

[21] Appl. No.: 816,183

[22] Filed: Jan. 6, 1986

[51] Int. Cl.$^4$ .................. C07C 17/26; C07C 19/08
[52] U.S. Cl. ................................ 570/139; 570/125
[58] Field of Search ........................ 570/172, 139

[56] References Cited

U.S. PATENT DOCUMENTS 2,788,375  4/1957  Ehrenfield ................... 570/172
4,740,640  4/1980  Boutevin et al. ............. 570/172

FOREIGN PATENT DOCUMENTS 201708   8/1982  Czechoslovakia ............ 570/172
93580    9/1983  European Pat. Off. ....... 570/172
115943   8/1984  European Pat. Off. ....... 570/172

OTHER PUBLICATIONS

Boutevin et al, Telomerization by Redox Catalysis–Part V, European Polymer Journal, vol. 12, pp. 1–18(1976)—Translation.

Primary Examiner—J. E. Evans
Attorney, Agent, or Firm—James F. Tao; James F. Mudd; Willaim G. Gosz

[57] ABSTRACT

Telomers are prepared by reacting chlorotrifluoroethylene with 1,2-dibromo-2-chlorotrifluoroethane (CBrClFCF$_2$Br) in the presence of a redox catalyst system comprising a metal halide selected from the group consisting of FeCl$_3$, FeBr$_3$, CuBr$_2$, CuCl$_2$, TiCl$_4$, VCl$_3$, and NiCl$_2$, and a reducing agent selected from the group consisting of Fe, Ni, Cu, Ti, V and benzoin. The preferred catalyst system is ferric chloride and nickel. The telomers of this invention have the structural formula

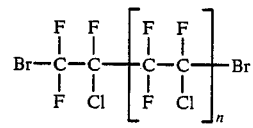

where n is in the range of 1 to 10, and are useful for preparing non-flammable hydraulic fluids.

3 Claims, No Drawings

TELOMERS PREPARED FROM CHLOROTRIFLUOROETHYLENE AND 1,2-DIBROMO-2-CHLOROTRIFLUOROETHANE

BACKGROUND OF THE INVENTION

The present invention relates to telomers of the formula

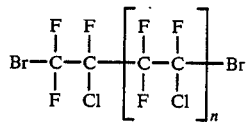

where n is in the range of 1 to 10, and processes for preparing such telomers. The telomers of this invention are saturated, low molecular weight polymers which are useful for preparing non-flammable hydraulic fluids.

Various methods of preparing chlorotrifluoroethylene ("CTFE") telomers are known in the prior art and have been practiced commercially for many years. An article by William T. Miller, Jr. et al in *Industrial and Engineering Chemistry*, pages 333–337 (1947), entitled "Low Polymers of Chlorotrifluoroethylene", describes a process for producing low molecular weight polymers of CTFE by polymerization in a solution of chloroform using benzoyl peroxide as a polymerization promoter. Other solvents disclosed in the reference as being useful for this purpose include carbon tetrachloride and tetrachloroethylene. The solution is heated in a pressure vessel for 1¾ hours at 100° C., and the unreacted CTFE monomer and chloroform are removed by distillation, leaving a crude telomer of general formula $CHCl_2(CF_2CClF)_nCl$, which can be further heated and distilled to yield products ranging from a light oil to a semi-solid wax or grease.

Another process for preparing low molecular weight CTFE polymers is described in U.S. Pat. No. 2,788,375, issued Apr. 9, 1957. This process comprises reacting CTFE with a saturated brominated compound in the presence of a source of radiation. Suitable brominated compounds include 1,2-dibromo-2-chlorotri-fluoroethane ($CF_2BrCClFBr$). The saturated bromopolychlorofluoro compounds obtained by this process can then be distilled, and the isolated fractions reacted with chlorine to prepare polychlorofluoro compounds. The compounds are predominantly higher molecular weight telomers, i.e. n is greater than 4.

Czechoslovakian Pat. No. 201,708, published Aug. 15, 1982, discloses the reaction of CTFE with $CBrClCF_2Br$ using a source of radiation at a temperature of from 20° C. to 30° C. to prepare 1,4-dibromo-2,3-dichlorohexafluorobutane and 1,6-dibromo-2,3,5-trichlorononafluorohexane as principal reaction products. These compounds are designated by the following structural formulas:

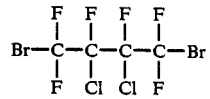

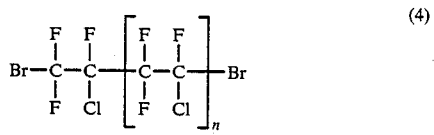

Both compounds (1) and (2) share the common feature of having the same end groups, i.e., —$CF_2Br$, as well as adjacent pairs of —CFCl-groups in the body of the telomer. Telomers having structures such as (1) and (2) are believed to be inherently more unstable and are less easily separated from impurities than the telomers of the present invention.

A more recent development in this field is described in a series of articles by Y. Pietrasanta et al entitled "Telomerization by Redox Catalysis" appearing in the *European Polymer Journal*, Vol. 12 (1976). This technology involves the reaction of single carbon halogenated telogens, such as $CCl_4$ and $CCl_3Br$, with CTFE in the presence of benzoin and a suitable redox catalyst, such as ferric chloride. The telomerization reaction is suitably carried out in acetonitrile which is a common solvent for the reactants and catalysts. The telomerization reaction can be illustrated as follows:

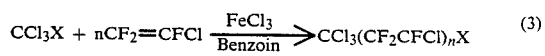

where X is chlorine or bromine. The reference further discloses that the use of $CCl_3Br$ as a telogen results in a lower degree of telomerization and a higher proportion of monoaddition product than with the use of $CCl_4$.

The redox process has the advantage of directly preparing low molecular weight products without the necessity of cracking or fractionating a higher molecular weight polymer.

A modification of the redox process is disclosed in commonly assigned European Patent Application No. 83302397.1, published Nov. 9, 1983. In this modification, nickel is substituted for benzoin in reaction (3). This process has the advantage of simplifying the reaction by eliminating the necessity for removing benzoin from the reaction mixture, whic is a time-consuming and costly operation. In addition, when telomers prepared using such a system are fluorinated, the resulting product does not contain unsatisfactory levels of unsaturation.

It is therefore a principal object of the present invention to provide a process for preparing novel CTFE telomers which can be readily separated into relatively pure isomers and which can be further chlorinated to prepare non-flammable hydraulic fluids.

SUMMARY OF THE INVENTION

In accordance with the present invention, telomers of the structural formula

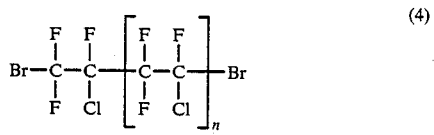

where n is in the range of 1 to 10, are prepared by reacting chlorotrifluoroethylene with 1,2-dibromo-2-chlorotrifluoroethane ($CBrClFCF_2Br$) in the presence of a redox catalyst system. The redox catalyst system comprises a reducible metal halide selected from the group consisting of $FeCl_3$, $FeBr_3$, $CuBr_2$, $CuCl_2$, $TiCl_4$, $VCl_3$ and $NiCl_2$, and a reducing agent selected from the group consisting of Fe, Ni, Cu, Ti, V and benzoin. The preferred catalyst system is ferric chloride and nickel. The reaction is conducted in a common solvent for the reactants and catalysts, preferably acetonitrile.

The telomer of formula $CF_2BrCFCl(CF_2CFCl)Br$, corresponding to an n value of 1, can be advantageously separated from the reaction product and recycled to the reaction mixture to increase the yield of products in the desired molecular weight range. Following separation of the telomers into component telomer species and chlorination to stabilize the telomer, the product is suitable for formulation as a non-flammable hydraulic fluid.

DESCRIPTION OF THE PREFERRED EMBODIMENTS

The telomerization process of the present invention involves the reaction of chlorotrifluoroethylene with 1,2-dibromo-2-chlorotrifluoroethane in a solvent, such as acetonitrile, in the presence of a catalytic amount of $FeCl_3$ and a suitable metal. This process can be illustrated as follows:

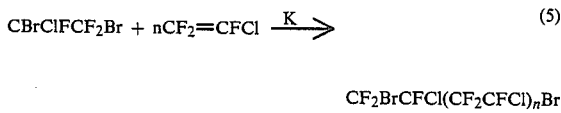

$$CF_2BrCFCl(CF_2CFCl)_nBr$$

where n is in the range of 1 to 10.

In reaction (5), K is a redox catalyst system comprising a metal halide selected from the group consisting of $FeCl_3$, $FeBr_3$, $CuBr_2$, $CuCl_2$, $TiCl_4$, $VCl_3$ and $NiCl_3$, and a reducing agent selected from the group consisting of iron, nickel, copper, titanium, vanadium and benzoin, where the reducing agent must be capable of reducing the metal halide selected. Typical combinations of metal halides and reducing agents which are operable include $FeCl_3$ or $FeBr_3$ and Fe or Ni, $TiCl_4$ and Ti, $CuCl_2$ or $CuBr_2$ and Cu, $NiCl_3$ and Ni, $VCl_3$ and V, and preferably $FeCl_3$ and Ni. Mixtures and alloys of the metal reducing agents are also operable in this invention. When K is a redox catalyst system as described above, reaction (5) is conducted in a common solvent such as acetonitrile, benzonitrile or propionitrile, and preferably acetonitrile.

In a further embodiment, dichloro-tris(triphenylphosphine) ruthenium (II) has also been found effective as the sole catalyst K in reaction (5). In this embodiment, a solvent is not required in the reaction mixture. Alternatively, catalyst K can also comprise a metal halide having a lower oxidation state such as, for instance, $FeCl_2$, $FeBr_2$, CuBr or CuCl, as the sole catalyst present.

Reaction (5) results in the preparation of a mixture of individual telomer species having molecular weights corresponding to n values of from 1 to 10, rather than pure isomers having a discrete structure, i.e a single n value. Separation of the individual telomer species from the mixture is accomplished by distillation using procedures well known to those skilled in this art.

The lighter molecular weight telomers i.e., telomers having an n value of 5 or less, generally predominate in reaction (5). Some of the lighter weight materials, such as the telomer corresponding to an n value of 1, have no intrinsic commercial value. However, other telomers are of considerable current interest. For instance, non-flammable hydraulic fluids require an average molecular weight corresponding to an n value intermediate between 2 and 4. These fluids can be produced by first preparing individual stabilized, i.e. chlorinated, telomers having n values between 2 and 4, and blending these telomers to obtain the desired viscosity. Control of the molecular weight distribution in reaction (5) is therefore essential since the most desirable products require a narrow molecular weight distribution. This can be achieved by maintaining the concentration of metal halide in the reaction mixture in the range of from about 0.01% to about 2% by weight of CTFE, and also maintaining the concentration of reducing agent in the reaction mixture in an amount of from about 0.5% to about 10% by weight of CTFE.

The preferred metal reducing agent is nickel and nickel alloys such as Hastelloy C (Hastelloy is registered trademark of the Union Carbide Corporation). The metal may be physically present in the reaction mixture in a variety of forms, such as a powder, particles of various sizes, wires, plates, or as a cladding material on the internal surface of the reactor. The preferred form is a finely divided powder which is uniformly dispersed in the reaction vessel by means of mechanical agitation, such as in a stirred reactor.

The telomerization reaction is preferably conducted in a stirred reactor under elevated temperature and pressure conditions, with temperatures generally ranging from about 70° C. to about 150° C., and pressures generally in the range of from about 75 psi to about 450 psi.

In one embodiment of this invention, the telomer having an n value of 1 is separated from the product mixture and returned to the telomerization reaction. This telomer then functions as a telogen in the same capacity as $CBrClFCF_2Br$. This serves to directly convert a reaction by-product of limited utility into a useful reactant.

The products of reaction (5) are novel compounds. These compounds are distinguished from related prior art compounds by the distribution of —$CF_2$— and —CFCl— groups in the telomer chain, and by the presence of one —$CF_2Br$ and one —CFClBr end group. These telomers can be represented by the following structure:

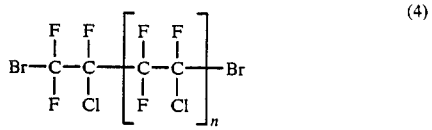

(4)

As indicated in formula (4), the telomers of the present invention do not have adjacent pairings of —CFCl— groups. Rather, the telomers of this invention are characterized by alternating pairs of —$CF_2$— and —CFCl— groups. It is theorized that the perceived instability of the prior art compounds is due to the presence of adjacent —CFCl— groups in the telomer which may result in cleavage of the telomer chain or a cleavage of the Cl—C bond. Therefore, the configuration of the telomers shown in formula (4) should be inherently more stable than the prior art telomers. Compare, for instance, formula (4) with formulas (1) and (2).

The existence of a —CClFBr and a —$CF_2Br$ group on each end of the telomer is particularly advantageous since it permits the selective chlorination and separation of relatively pure isomers. The particular configuration of the end groups of the telomers of this invention is surprising since it indicates that the —CFClBr group of the telogen of this invention (CF₂BrCFClBr) is more reactive that the —CF₂Br group. This is unexpected and surprising in view of the known reactivity o the —CF₂Br group for related telogens, such as CF₂BrCF₂Br, in analogous telomerization reactions. Compare the results of Examples 1 and 4 below which illustrate the reactivity of both telogens.

The structure of the telomers of formula (4), and particularly the relative placement of the —(CF₂—CFCl)$_n$— group and its components, has been confirmed by NMR spectroscopy. The photochemical processes of the prior art which employ analogous or equivalent reactants surprisingly do not result in the preparation of compounds having this structure.

The following examples are intended to further illustrate the varius embodiments and advantages of the present invention without limiting it thereby. These examples illustrate the preparation of CTFE telomers using various telogens and telomerization processes.

EXAMPLE 1

A one gallon glass-lined agitated reactor having a jacket of circulating pressurized water for heating and cooling was charged with 1200 grams of CBrClFCBrF₂, 756 grams of acetonitrile, 5 grams of ferric chloride and 40 grams of nickel powder. The reactor was closed and pressure tested. 1403 grams of CTFE was added to the reactor from a pressurized reservoir. The reactor was then heated to 112° C. over a 43 minute period and held at this temperature for 9 hours. During this time, the pressure dropped to 240 psi from a maximum of 308 psi.

After cooling, the unreacted CTFE was bled off. The crude reaction mixture was washed with dilute HCl and then water. Gas chromatographic analysis indicated that 52% of the CBrClFCBrF₂ had reacted.

After distilling off the acetonitrile and unreacted telogen, 1024 grams of product was obtained. Gas chromotographic analysis of this product revealed the following distribution of telomers in the indicated amounts:

| Telomer | Amount (%) |
| --- | --- |
| CF₂BrCFCl(CF₂CFCl)Br | 20.7 |
| CF₂BrCFCl(CF₂CFCl)₂Br | 18.6 |
| CF₂BrCFCl(CF₂CFCl)₃Br | 16.9 |
| CF₂BrCFCl(CF₂CFCl)₄Br | 13.3 |
| CF₂BrCFCl(CF₂CFCl)₅Br | 9.3 |
| CF₂BrCFCl(CF₂CFCl)₆Br | 5.3 |
| CF₂BrCFCl(CF₂CFCl)₇Br | 2.5 |
| Other | 13.4 |

The first telomer, CF₂BrCFCl(CF₂CFCl)Br, was isolated by distillation (b.p. 86° C. at 47 mm. Hg.). NMR analysis of this material confirmed the following structure:

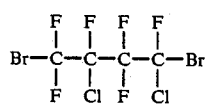

Similarly, NMR analysis of the next three higher telomers confirmed the following structures:

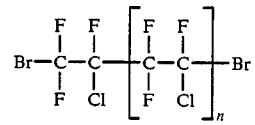

n = 2, 3 and 4

EXAMPLE 2

A cylindrical reactor having an inner quartz light well fitted with a 400 W medium pressure mercury vapor lamp was charged with 1033 grams of 1,2-dibromo-2-chlorotrifluoroethane. The reactor was equipped with a magnetically driven agitator and vented through a dry-ice condenser. A gas inlet tube extended to near the bottom of the reactor, and the assembly was cooled by immersion in a refrigerated bath.

CTFE was introduced at such a rate that the mixture was maintained saturated, as evidenced by a slow reflux from the condenser. The light was turned on. With the cooling bath at $-5°$ C., the reaction temperature was 35° C. due to the heat evolved by the lamp.

After 26.5 hours, the reaction was stopped. The composition of the reaction mixture was determined by G.C. analysis to be:

| Telomer | Amount (%) | |
| --- | --- | --- |
| CF₂BrCFClBr | 77.2 | |
| 4 Carbon Telomer | 10.2 | (2 components) |
| 6 Carbon Telomer | 6.3 | (4 components) |
| 8 Carbon Telomer | 3.2 | (2 components) |
| 10 Carbon Telomer | 1.4 | (2 components) |
| 12 Carbon Telomer | 0.4 | |

The mixture of the two isomers comprising the 4 carbon telomer was isolated by distillation (b.p. 80° C. at 40 mm. Hg.). NMR analysis indicated that neither component was the same as the corresponding telomer of Example 1, i.e. CF₂BrCEFCl(CF₂CFCl)Br.

EXAMPLE 3

100 Grams of 1,2-dibromo-2-chlorotrifluoroethane and 3 grams of benzoyl peroxide were placed in the glass liner of a 350 ml stirred autoclave. After flushing with nitrogen, 107 grams of CTFE was added. The autoclave was closed and slowly heated to 115° C. At this temperature an exotherm resulted which caused the temperature to increase to 154° C., even though cooling was applied. Once the temperature fell to 115° C., the reaction was maintaied at this temperature for four hours. Additional CTFE was introduced to maintain the pressure of 200 p.s.i. It was then cooled to room temperature, and unreacted CTFE was vented off.

Upon opening the autoclave, a viscous product which contained a considerable amount of a white solid was obtained. GC analysis of the liquid portion showed that only trace amounts of telomers were formed. Some relatively low molecular weight products were formed, however, but these products were not further characterized.

EXAMPLE 4

The procedure of Example 1 was repeated using the one gallon glass-lined agitated reactor charged with 1130 grams of CF₂BrCF₂Br, 756 grams of acetonitrile, 1572 grams of chlorotrifluoroethylene, 5 grams of ferric chloride and 40 grams of nickel powder. During the 9 hour reaction at 112° C., the pressure decreased from a maximum of 339 psi to 268 psi. The total pressure drop was approximately the same as in Example 1 indicating that approximately the same amount of CTFE was consumed.

The crude product recovered after cooling and venting the unreacted CTFE contained an appreciable amount of solids. The solids were filtered off and dried for several days and found to weigh 490 grams. These solids were insoluble in common solvents.

Due to the large amount of solids formed, the gas chromatographic analysis of the liquid portion of the reaction mixture could not be made on a quantitative basis. Based on the high molecular weight material or polymer formed, it is evident that only traces, if any, of telomers in the useful molecular weight range were formed, i.e. where n is 5 or less. The $CF_2BrCF_2Br$ reactant is sufficiently volatile that some of it was lost during venting of the reactor, thus preventing an accurate estimate of the degree of conversion.

EXAMPLE 5

100 Grams of $CF_2BrCFCl(CF_2CFCl)Br$, 64 grams of acetonitrile, 0.25 grams of $FeCl_3$ and 2 grams of nickel powder were placed in the glass liner of a 350 ml. stirred autoclave. After flushing with nitrogen, 166 grams of chlorotrifluoroethylene was added. The autoclave was closed and slowly heated to 110° C. The reaction was maintained at this temperature for 16 hours. Additional CTFE was introduced to maintain the pressure at 115 psi. It was then cooled to room temperature, and unreacted CTFE vented off.

Upon opening the autoclave, a reaction mixture which consisted of two liquid phases was obtained. This reaction mixture was washed with dilute HCl and then with water. GC analysis of the washed material indicated that 76% of the $CF_2BrCFCl(CF_2CFCl)Br$ had reacted. The telomers formed had the same distribution as those formed using 1,2-dibromo-2-chlorotrifluoro ethane as a starting material.

EXAMPLE 6

100 Grams of 1,2-dibromo-2-chlorotrifluoroethane, 63 grams of acetonitrile, 2 grams of $CuBr_2$ and 1.5 grams of copper powder were placed in the glass liner of a 350 ml. stirred autoclave. After flushing with nitrogen, 124 grams of CTFE was added. The autoclave was closed and slowly heated to 120° C. The reaction was maintained at this temperature for 4 hours. Additonal CTFE was introduced to maintain the pressure at 200 psi. It was then cooled to room temperature, and unreacted CTFE vented off. The reaction mixture was washed with dilute HCl and then with water. GC analysis of the washed material indicated that 12% of the telogen had reacted. The telomers formed had a flatter distribution than those of Example 1, and there were less by-products present.

EXAMPLE 7

100 Grams of 1,2-dibromo-2-chlorotrifluoroethane, 63 grams of acetonitrile, 2.7 grams of $FeBr_3$, and 1.5 grams of iron powder were placed in the glass liner of a 350 ml. stirred autoclave. After flushing with nitrogen, 115 grams of CTFE was added. The autoclave was closed and slowly heated to 115° C. The reaction was maintained at this temperature for 4 hours. Additional CTFE was introduced to maintain the pressure at 200 psi. It was then cooled to room temperature, and unreacted CTFE vented off. The reaction mixture was washed with dilute HCl and then with water. GC analysis of the washed material indicated that 14% of the telogen had reacted. The telomer mixture was composed of 60% of $CF_2BrCFCl(CF_2CFCl)Br$.

EXAMPLE 8

100 Grams of 1,2-dibromo-2-chlorotrifluoroethane, 63 grams of acetonitrile, 2 grams of $TiCl_4$ and 1.5 grams of titanium powder were placed in the glass liner of a 350 ml. stirred autoclave. After flushing with nitrogen, 114 grams of CTFE was added. The autoclave was closed and slowly heated to 115° C. The reaction was maintained at this temperature for 4 hours. Additional CTFE was introduced to maintain the pressure at 200 psi. It was then cooled to room temperature, and unreacted CTFE vented off. The reaction mixture was washed with dilute HCl and then with water. GC analysis of the washed material indicated that 16% of the telogen had reacted. The distribution of the telomers formed was shifted toward the lower molecular weight range as compared to the distribution of telomers in Example 1.

EXAMPLE 9

100 Grams of 1,2-dibromo-2-chlorotrifluoroethane, 60 grams of acetonitrile, 1.5 grams of $VCl_3$ and 1.5 grams of vanadium powder were placed in the glass liner of a 350 ml. stirred autoclave. After flushing with nitrogen, 112 grams of CTFE was added. The autoclave was closed and slowly heated to 120° C. The reaction was maintained at this temperature for 4 hours. Additional CTFE was introduced to maintain the pressure at 200 psi. It was then cooled to room temperature, and unreacted CTFE vented off. The reaction mixture was washed with dilute HCl and then with water. GC analysis of the washed material indicated that 5% of the telogen had reacted. The telomers formed had a flatter distribution than those of Example 1.

EXAMPLE 10

100 Grams of 1,2-dibromo-2-chlorotrifluoroethane, 63 grams of acetonitrile, 1.5 grams of $CuBr_2$ and 2 grams of benzoin were placed in the glass liner of a 350 ml. stirred autoclave. After flushing with nitrogen, 113 grams of CTFE was added. The autoclave was closed and slowly heated to 120° C. The reaction was maintained at this temperature for four hours. Additional CTFE was introduced to maintain the pressure at 200 psi. It was then cooled to room temperature, and unreacted CTFE vented off. The reaction mixture was washed with dilute HCl and then with water. GC analysis of the washed material indicated that 20% of the telogen had reacted. The product contained more impurities than that of Example 1.

EXAMPLE 11

100 Grams of 1,2-dibromo-2-chlorotrifluoroethane, 63 grams of acetonitrile, 1.5 grams of $FeCl_3$ and 2 grams of benzoin were placed in the glass liner of a 350 ml. stirred autoclave. After flushing with nitrogen, 122 grams of CTFE was added. The autoclave was closed and slowly heated to 120° C. The reaction was maintained at this temperature for 4 hours. Additional CTFE was introduced to maintain the pressure at 200 psi. It was then cooled to room temperature, and unreacted CTFE vented off. The reaction mixture was washed with dilute HCl and then with water. GC analysis of the washed material indicated that 15% of the telogen had reacted. The product contained more impurities than that of Example 1, but less than Example 10.

EXAMPLE 12

100 Grams of 1,2-dibromo-2-chlorotrifluoroethane, 60 grams of benzonitrile, 1.5 grams FeCl₃ and 1.5 grams of nickel powder were placed in the glass liner of a 350 ml. stirred autoclave. After flushing with nitrogen, 111 grams of CTFE was added. The autoclave was closed and slowly heated to 120° C. The reaction was maintained at this temperature for 4 hours. Additional CTFE was introduced to maintain the pressure at 200 psi. It was then cooled to room temperature, and unreacted CTFE vented off. The reaction mixture was washed with dilute HCl and then with water. GC analysis of the washed material indicated that 50% of the telogen had reacted. The telomers formed had a distribution similar to those of Example 1.

EXAMPLE 13

100 Grams of 1,2-dibromo-2-chlorotrifluoroethane, 60 grams of propionitrile, 1.5 grams of FeCl₃ and 1.5 grams of nickel powder were placed in the glass liner of a 350 ml. stirred autoclave. After flushing with nitrogen, 113 grams of CTFE was added. The autoclave was closed and slowly heated to 120° C. The reaction was maintained at this temperature for 4 hours. Additional CTFE was introduced to maintain the pressure at 200 psi. It was then cooled to room temperature, and unreacted CTFE vented off. The reaction mixture was washed with dilute HCl and then with water. GC analysis of the washed material indicated that 12% of the telogen had reacted. The telomers formed had a distribution shifted toward the low molecular weight products as compared to telomers of Example 1.

EXAMPLE 14

100 Grams of 1,2-dibromo-2-chlorotrifluoroethane, 60 grams of DMSO, 1.5 grams of FeCl₃ and 1.5 grams of nickel powder were placed in the glass liner of a 350 ml. stirred autoclave. After flushing with nitrogen, 113 grams of CTFE was added. The autoclave was closed and slowly heated to 120° C. The reaction was maintained at this temperature for 4 hours. Additional CTFE was introduced to maintain the pressure at 200 psi. It was then cooled to room temperature, and unreacted CTFE vented off. The reaction mixture was washed with dilute HCl and then with water. After stripping of unreacted telogen, the crude product weighed 12 g. It contained more by-products that the crude product of Example 1.

EXAMPLE 15

50 Grams of 1,2-dibromo-2-chlorotrifluoroethane and 1.5 grams of dichloro-tris(triphenylphosphine) ruthenium (II) were placed in the glass liner of a 350 ml. stirred autoclave. After flushing with nitrogen, 112 grams of CTFE was added. The autoclave was closed and slowly heated to 140° C. The reaction was maintained at this temperature for 4 hours. It was then cooled to room temperature, and unreacted CTFE vented off. The reaction mixture was washed with dilute HCl and then with water. GC analysis of the washed material indicated that 27% of the telogen had reacted. The telomers formed had a flatter distribution than those of Example 1. The individual telomers did not appear to be contaminated by isomers.

While various embodiments and exemplifications of this invention have been shown and described in the specification, modifications and variations thereof will be readily appreciated by those skilled in the art. It is to be understood, therefore, that the appended claims are intended to cover all such modifications and variations which are considered to be within the scope and spirit of the present invention.

What is claimed is:

1. A process for preparing a distribution of telomers of structural formula

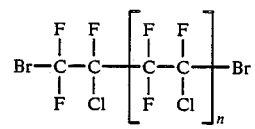

where n is in the range of 1 to 10, said telomer being further characterized by the absence of adjacent —CFCl— groups, comprising reacting chlorotrifluoroethylene with CBrClCF₂Br in the presence of a catalyst system comprising CuBr₂ and copper, said reaction being conducted in a common solvent for the reactants and catalysts.

2. A process for preparing a distribution of telomers of structural formula

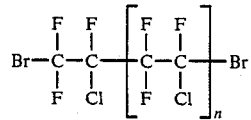

where n is in the range f 1 to 10, said telomer being further characterized by the absence of adjacent —CFCl— groups, comprising reacting chlorotrifluoroethylene with CBrClCF₂Br in the presence of a catalyst system comprising TiCl₄ and titanium, said reaction being conducted in a common solvent for the reactants and catalysts.

3. A process for preparing a distribution of telomers of structural formula

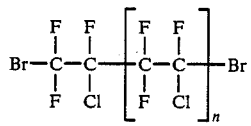

where n is in the range of 1 to 10, said telomer being further characterized by the absence of adjacent —CFCl— groups, comprising reacting chlorotrifluoroethylene with CBrClCF₂Br in the presence of a catalyst system comprising VCl₃ and vanadium, said reaction being conducted in a common solvent for the reactants and catalysts.

* * * * *